(12) United States Patent
Zhang

(10) Patent No.: US 9,272,012 B1
(45) Date of Patent: Mar. 1, 2016

(54) HERBAL SKIN CARE COMPOSITION

(71) Applicant: Nefeli Corp., Port Washington, NY (US)

(72) Inventor: Ping Zhang, Port Washington, NY (US)

(73) Assignee: Nefeli Corp., Port Washington, NY (US)

( * ) Notice: Subject to any disclaimer, the term of this patent is extended or adjusted under 35 U.S.C. 154(b) by 0 days.

(21) Appl. No.: 14/925,573

(22) Filed: Oct. 28, 2015

Related U.S. Application Data

(63) Continuation of application No. 13/618,187, filed on Sep. 14, 2012, now Pat. No. 9,192,643.

(60) Provisional application No. 61/534,818, filed on Sep. 14, 2011.

(51) Int. Cl.
  *A61K 36/00* (2006.01)
  *A61K 36/8984* (2006.01)
  *A61K 36/898* (2006.01)

(52) U.S. Cl.
  CPC ........... *A61K 36/8984* (2013.01); *A61K 36/898* (2013.01)

(58) Field of Classification Search
  None
  See application file for complete search history.

(56) References Cited

U.S. PATENT DOCUMENTS

| 2010/0255076 A1 | 10/2010 | Heber et al. |
| 2010/0267659 A1 | 10/2010 | Sasaki et al. |
| 2011/0002968 A1 | 1/2011 | Leplanquais et al. |
| 2012/0064021 A1 | 3/2012 | Leplanquais et al. |

FOREIGN PATENT DOCUMENTS

| CN | 1726993 | 2/2006 |
| CN | 101849957 | 10/2010 |
| JP | 2002205933 | 7/2002 |
| JP | 20110200948 | 2/2011 |
| KR | 10-2009-0083082 | 8/2009 |
| KR | 10-2009-0083083 | 8/2009 |
| WO | WO 2009/102880 | 8/2009 |

OTHER PUBLICATIONS

Hsie, et al., "Structure and bioactivity of the polysaccharides in medicinal plant Dendrobium huoshanense", Bioorganic & Medicinal Chemistry (2008), 16(11), 6054-6068.
Lu, et al., "Progress in physiological and biochemical characters of Dendrobium huoshanense", Chinese Traditional and Herbal Drugs, vol. 37, No. 5, May 2006.
Zha et al., "Study on Antioxidant Activity of Polysaccharides from *Dendrobium* Species," Food Science, 2007, vol. 28, No. 10.

*Primary Examiner* — Qiuwen Mi
(74) *Attorney, Agent, or Firm* — Cesari and McKenna LLP

(57) ABSTRACT

Described herein is a method of treating aging skin in a subject, the method comprising applying a topical skin care composition to a surface of the skin of the subject in need thereof, the composition containing a whole plant extract solution of *Dendrobium Huoshanense*.

13 Claims, No Drawings

HERBAL SKIN CARE COMPOSITION

CROSS-REFERENCE TO RELATED APPLICATION

This application is a continuation of U.S. patent application Ser. No. 13/618,187, filed on Sep. 14, 2012, which claims priority to U.S. Provisional Application No. 61/534,818, filed on Sep. 14, 2011. The contents of both prior applications are hereby incorporated by reference herein in their entirety.

BACKGROUND

Aging of skin results from a combination of intrinsic factors, e.g., genetic factors, and extrinsic factors, e.g., environmental factors such as sun damage and smoking. Aging of skin takes place at the microscopic and biochemical level, and manifests outwardly as various signs, e.g., wrinkles, dryness, roughness, dullness, brown/dark/age spots, and sagging of the skin.

Although a number anti-aging skin care products are commercially available, synthetic ingredients in many of these products may be harsh, irritating or even harmful to the skin or the user over time. Consumers are seeking skin care products that are not only natural but also effective with little or no side effects.

SUMMARY

This invention is based on the unexpected discovery that an extract solution of *Dendrobium Huoshanense* can reduce signs of skin aging when applied topically.

Accordingly, described herein is a topical skin care composition containing an extract solution of *Dendrobium Huoshanense* and one or more topical carriers. The extract solution can be obtained by extracting dried *Dendrobium Huoshanense* with a solvent, the ratio of the dried *Dendrobium Huoshanense* to the extract solution being 0.1:100 to 7:100 by weight.

In another aspect, also contemplated herein is a method of treating aging of skin in a subject using the above-described topical skin care composition. For example, the composition can be used to treat, reduce, or improve one or more signs of aging, e.g. wrinkles, dryness, roughness, dullness, blotchiness, brown/dark/age spots, blemishes, and/or skin sagging.

The details of one or more embodiments of the invention are set forth in the accompanying drawing and the description below. Other features, objects, and advantages of the invention will be apparent from the description and drawing, and from the claims.

DETAILED DESCRIPTION

Described herein is a topical skin care composition that includes an extract solution of *Dendrobium Huoshanense* and one or more topical carriers. This composition can be used to treat aging of the skin.

*Dendrobium Huoshanense* is one species of *Dendrobium*. *Dendrobium* is a large genus of orchids that originate mainly in tropical and subtropical Asia, Australia, and the Pacific islands. There are around 1000 different species globally. Among these 1000 species, 76 species can be found in China, most of them being naturally located in southwestern and southern China and Taiwan. *Dendrobium Huoshanense*, one of the 76 species, grows primarily on ancient tree branches or rock cliffs at very high altitudes in the Dabie Mountain area of Huoshan, Anhui province.

*Dendrobium Huoshanense* is an herbal used in Traditional Chinese Medicine. Extracts of *Dendrobium Huoshanense* are traditionally administered orally to patients for various purposes, e.g., release or alleviate thirst, awaking the spleen (which, in Traditional Chinese Medicine, means to strengthen the digestive system), release summer heat from the body, increase the body's energy, preserve health, and promote longevity. It has also been used orally to fight fatigue, nourish the visceral system, relieve dryness, calm wheezing, brighten eyes, and restores the voice. Recently, *Dendrobium Huoshanense* has been demonstrated to have antitumor and blood sugar lowering effects.

An extract solution of *Dendrobium Huoshanense*, as that term is used herein, refers to an extract solution obtained by extracting *Dendrobium Huoshanense* plant material with a solvent, the ratio of the plant material to the final extract solution being 0.1:100 to 7:100 by weight, e.g., 1:20 or 1:100. For example, the extract solution can be prepared by using 0.1 g to 7 g of dried *Dendrobium Huoshanense* to create 100 g of herbal extract solution. A skilled practitioner would readily appreciate that the solvent used for extraction should be suitable for application to the skin of a subject, e.g., a human patient. The *Dendrobium Huoshanense* plant material used can be in the form of whole dried plant, crushed herb, or powdered herb.

The extract solution of *Dendrobium Huoshanense* can be obtained by various conventional methods. Such methods include, but are not limited to, soaking, boiling, extracting by an soxhlet extractor, pressure cooking, or infusing *Dendrobium Huoshanense* plant material in various media. The media include, but are not limited to, water, alcohols (e.g. ethanol and isopropanol), other organic solvents (e.g. acetone, hexane, diethyl ether, and petroleum ether), oil, and combinations of such extraction media. After extraction, the extract solution can be separated from the solid by sieving, filtering, pressing or another suitable method. The extract solution of *Dendrobium Huoshanense* thus prepared can be used as is without further treatment or modification, e.g., fermentation. Alternatively, the extract solution can be further treated, for example, by adding rice and yeast to ferment the solution. The fermented mixture can then be filtered to remove the solid material.

Described in Example 1 below is an exemplary method of extraction using 1 g of dried *Dendrobium huosanese*. It should be noted that this method can be altered in a wide variety of ways, such as increasing or decreasing the soaking and/or boiling times, changing the solvent, increasing or decreasing the number of boiling steps, substituting other extraction techniques for boiling and/or soaking, eliminating or switching the order of steps, and substituting blending with other methods of grinding, crushing, pulverizing or mixing an herbal/solvent mixture.

The topical skin care composition described herein can contain about 0.01%-25% by weight of an extract solution of *Dendrobium Huoshanense*, including 0.05%, 0.1%, 0.5%, 1%, 2%, 3%, 4%, 5%, 6%, 7%, 8%, 9%, 10%, 12% 15%, 20%, and 25%. For example, the composition can contain 1%-25% of the extract solution.

In addition, the topical skin care composition includes one or more excipients, vehicles, or media known in the art for topical administration. As used herein, the term "topical carrier" or "topical excipient" refers to an ingredient that is not suitable for oral administration. A topical carrier can be used, for example, to formulate the composition in a particular form (e.g., cream), or to enhance the feel, color, scent, absorbability, or spreadability of the composition. For example, the skin care composition can include ingredients that are found in a cosmetic formulation, such as pigments, fragrances, preservatives, protectives, adsorbents, demulcents, emollients, buffering agents, skin-penetration agents, and surfactants. In some embodiments, the topical skin care composition also contains one or more other skin care ingredients, e.g., sunscreens, antioxidants, vitamins, oils, fermented rice and/or other herbals. The types and amounts of the above-discussed optional ingredients can be determined by one of ordinary skill in the art based upon general knowledge in the skin care formulation art.

The topical skin care composition described above can be formulated as a cream, moisturizer, lotion, aqueous gel, non-aqueous gel, serum, mask, ointment, liquid, foam, spray, or any other form suitable for topical application.

Data described below show that an extract solution of *Dendrobium Huoshanense* effectively reduced or improved various signs of skin aging. Accordingly, the above-described topical skin care composition is useful for treating aging of skin. For example, the composition can be used to prevent, reduce, slow, alleviate, correct, or improve one or more signs of aging, e.g. wrinkles, dryness, roughness, dullness, blotchiness, brown/dark/age spots, blemishes, and skin sagging.

The skin care composition can be applied to various areas of the skin, e.g., face, neck, décolletage, hands, and feet, as needed. In some embodiments, the composition is applied once or twice daily. A skilled practitioner would readily recognize that the frequency of use depends on the needs of the user, the condition of the user's skin, and other factors known in the skin care arts.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are herein incorporated by reference in their entirety.

Example 1

Preparation of an *Dendrobium Huoshanense* Extract Solution

One gram of dried *Dendrobium Huoshanense* herbal was placed in 750 ml of water. The herbal was soaked for a minimum of 12 hours at room temperature. The mixture was then brought to a boil and then allowed to cool to 115-120° F. The entire mixture was then blended in a blender or similar apparatus. The blended mixture was then boiled for about 30 minutes at low heat, i.e., simmered, and then cooled to room temperature. The mixture was blended again in a blender or similar apparatus. The above series of simmering, cooling, and blending steps was repeated two more times. The liquid was then separated from the solid in the blended mixture by sieving, filtering, pressing, or another suitable method. The liquid was then evaporated by boiling to reduce its volume to about 100 ml (about 100 g by weight). This resulting liquid, i.e., a *Dendrobium Huoshanense* extract solution, can be used as is to make a skin care formulation.

Example 2

Effects of an *Dendrobium Huoshanense* Extract Solution on Signs of Skin Aging

Three patients were treated topically with a *Dendrobium Huoshanense* extract solution prepared from dried *Dendrobium Huoshanense* using the procedure described in Example 1 above. The ratio of the dried *Dendrobium Huoshanense* to the final extract solution was 1:20 by weight.

(A) Patient A

Patient A was a 46-year-old female complaining of having dry skin, and fine lines and wrinkles on her face, especially around the eye and mouth area. Patient A also complained about unevenness and dullness of complexion.

Patient A's initial clinical observations included: (1) blotchiness, redness, and irritation around the nose area and across both checks, as well as chin area; (2) dry skin all over the face with wrinkles around the eye and lip area (smoker lines); (3) dark spots all over the face, especially on the left cheek; (4) uneven skin tone in chin and cheek areas; and (5) rough skin and sagging in the cheek area.

Patient A was prescribed the 1:20 extract solution of *Dendrobium Huoshanense*. She was instructed to apply the extract twice daily, i.e., 10 drops in the morning and 10 drops in the evening, on clean face. Patient A followed the regiment for six weeks.

The results of the six-week clinical trial are summarized below.

The frown lines on Patient A's forehead have decreased in length and depth. The nasal folds and smile lines along the left side of the mouth have decreased in length and depth.

There was a decrease in sagging of skin. Overall skin tone was improved. There was also a significant reduction in irritation and redness.

The upper eyelid of her left eye showed lifting, less sagging, and significantly diminished appearance of fine lines.

There was less roughness and smoother skin under the eyes, particularly under the right eye.

There was an overall improvement in skin tone, dullness, blotchiness, and appearance of dark spots.

Data were also obtained from Image Pro I, an imaging device and skin care analysis system. RBG spots and UV spots were measured for each captured image. Results were from comparisons of images captured on the start and end dates of the six week trial. The data showed improvements in both RBG spots and UV spots.

Patient A indicated significant improvements in the following areas: wrinkles around the eyes and mouth, sagging skin in chin and neck area, age spots, discoloration, dark spots, dull skin, suppleness, and skin texture.

Patient A's comments included: "skin feels smoother and more regular in texture," "dark spots going away—especially (on) left cheek," "skin feels more supple and fewer wrinkles and sagging,"

(2) Patient B

Patient B was a 58-year-old female with complaints of overall sagging of face, deep wrinkles, blotchiness and redness of skin, dry skin with roughness especially in the chin area, sagging of the cheek, chin and eyelid area, and a sallow and dull complexion.

Patient B's initial clinical observations included: (1) rough and dry skin; (2) redness, blotchiness and irritation, especially around nose area and on both cheek areas; (3) sagging of face, including eyelids, cheek, and chin area; (4) deep wrinkles in forehead area, eyebrow area, outside of eye (i.e., crows feet), upper lip area (i.e., smoker line), and nasal labial folds.

Patient B was prescribed the 1:20 extract solution of *Dendrobium Huoshanense*. She was instructed to apply the extract twice daily, i.e., 10 drops in the morning and 10 drops in the evening, on clean face. Patient B followed the regiment for eight weeks.

The results of the eight-week clinical trial are summarized below.

The frown lines on Patient B's forehead have decreased in length and depth.

The ridges on bridge of nose were less significant in depth, and there was a decreased appearance of fine lines.

Patient B's upper eyelids showed lifting, less sagging, and a significant reduction of fine lines.

The crows feet along her right eye have diminished significantly. The fine lines have significantly reduced in depth and length.

The nasal folds and smile lines along the right side of Patient B's mouth have decreased in length and depth. The skin tone has improved, and there was visibly reduced irritation and redness of the cheek and nose area.

The smoker lines above her upper lip have flattened out.

The chin showed less sagging, skin tightening, less roughness, and diminished fine lines.

An overall reduction of wrinkles, better hydration of skin, and improvement of skin tone, dullness, blotchiness, and appearance of dark spots were observed.

Data were also obtained from Image Pro I. RBG spots and UV spots were measured for each captured image. Results were from comparisons of images captured on the start and end dates of the trial. The data showed improvements in both RBG spots and UV spots.

Patient indicated significant improvements in the following aspects: wrinkles, sagging skin, age spots/discoloration, skin texture, rosacea, dark spots, irritated skin, dry patches/spots, redness, dull skin, radiance, suppleness, and lifting around the eye.

Patient's comments included: "My skin in particular became softer than I have ever experienced. People commented how soft and radiant it looks. There is a brightness and radiance and highly toned, I had irritation across bridge of nose that dissipated and I was very pleased with this procedure." "There is less wrinkles, more firmness and improvement in dark spots," "skin is more hydrated".

(3) Patient C

Patient C was a 68-year-old female complaining of roughness and unevenness of the skin of her face, dry skin with large skin pores, overall facial sagging especially in the upper eyelids, cheek and chin area, deep wrinkles, and dark/age spots all over her face especially under both eyes.

Patient C's initial clinical observations included: (1) overall facial roughness and loose skin, (2) sagging in her upper eyelids, cheek and chin, (3) slight irritation and blotchiness on both cheeks, (4) deep nasal labial lines extending to chin area with puffiness by jaw, (5) wrinkles on her forehead, around the eyes, upper lip, cheek, and chin area, (6) unevenness of skin, (7) dark/age spots on her forehead, nose, and cheeks, (8) dull skin, and (9) blackheads.

Patient C was prescribed the 1:20 extract solution of *Dendrobium Huoshanense*. She was instructed to apply the extract twice daily, i.e., 10 drops in the morning and 10 drops in the evening, on clean face. Patient C followed the regiment for eight weeks.

The results of the eight-week clinical trial are summarized below.

The frown lines on Patient C's forehead have decreased in length and depth.

The ridges on the bridge of her nose were significantly reduced in depth. There was also a significant decrease in the appearance of fine lines in that area.

The upper eyelids showed lifting, less sagging, and diminished appearance of fine lines. The crows feet along the left eye and the right eye have significantly diminished.

An overall reduction of wrinkles, better hydration of skin, and improvement in skin tone, dullness, blotchiness, and dark spots were observed.

Data were also obtained from Image Pro I. RBG spots and UV spots were measured for each captured image. Results were from comparisons of images captured on the start and end dates of the trial. The data showed improvements in both RBG spots and UV spots.

Patient C indicated significant improvements in the following aspects: overall wrinkles, wrinkles and lifting around the eyes, sagging skin, age spots/discoloration, skin texture, dark spots, dry patches/spots, redness, dull skin, radiance, and suppleness.

Patient C's comments include: "I could not believe the change in my skin. I became soft, smooth and radiant. I feel that this is a product I would want to use every day. I have less wrinkles, more firmness and very moist."

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of treating aging skin in a subject, the method comprising applying a topical skin care composition to a surface of the skin of the subject in need thereof, the composition containing a whole plant extract solution of *Dendrobium Huoshanense*, wherein the extract solution is obtained by extracting a dried whole *Dendrobium Huoshanense* plant with a solvent, the ratio of the dried whole *Dendrobium Huoshanense* plant to the extract solution being 0.1:100 to 7:100 by weight.

2. The method of claim 1, wherein the extract solution is unfermented.

3. The method of claim 1, wherein the ratio of the dried whole *Dendrobium Huoshanense* plant to the extract solution is 1:100 to 1:20 by weight.

4. The method of claim 1, wherein the composition contains the extract solution in the range of 0.01%-25% by weight.

5. The method of claim 1, wherein the dried whole *Dendrobium Huoshanense* plant is extracted with water as the only solvent.

6. The method of claim 1, wherein the surface of the skin has wrinkles, blemishes, dryness, roughness, dullness, brown spots, dark spots, age spots, or sagging.

7. The method of claim 1, wherein the composition further contains a topical carrier.

8. The method of claim 7, wherein the composition is a cream, moisturizer, lotion, aqueous gel, non-aqueous gel, serum, mask, ointment, foam, or spray.

9. The method of claim 8, wherein the ratio of the dried whole *Dendrobium Huoshanense* plant to the extract solution is 1:100 to 1:20 by weight.

10. The method of claim 8, wherein the composition contains the extract solution in the range of 0.01%-25% by weight.

11. The method of claim 8, wherein the surface of the skin has wrinkles, blemishes, dryness, roughness, dullness, brown spots, dark spots, age spots, or sagging.

12. The method of claim 1, wherein the composition further includes an ingredient selected from the group consisting of a pigment, fragrance, preservative, protective, adsorbent, demulcent, emollient, buffering agent, skin-penetration agent, surfactant, sunscreen, and oil.

13. The method of claim 1, wherein the extract solution is obtained by a process including:
(1) soaking a dried whole *Dendrobium Huoshanense* plant in water for at least twelve hours at room temperature to obtain a mixture;
(2) boiling and then cooling the mixture to 115-120° F. to obtain a cooled mixture;
(3) blending, grinding, crushing, or pulverizing the cooled mixture to obtain a blended mixture;
(4) simmering and then cooling the blended mixture to room temperature to obtain a cooled blended mixture;
(5) repeating steps (3) and (4);
(6) removing solids from the cooled blended mixture to obtain an extract solution; and
(7) concentrating the extract solution.

\* \* \* \* \*